United States Patent [19]

Dransfield

[11] Patent Number: 5,104,352
[45] Date of Patent: Apr. 14, 1992

[54] MONITORING MEAT QUALITY

[75] Inventor: Eric Dransfield, Avon, England

[73] Assignee: National Research Development Corporation, London, England

[21] Appl. No.: 623,445

[22] PCT Filed: Apr. 18, 1990

[86] PCT No.: PCT/GB90/00586

§ 371 Date: Dec. 4, 1990

§ 102(e) Date: Dec. 4, 1990

[87] PCT Pub. No.: WO90/12507

PCT Pub. Date: Nov. 1, 1990

[30] Foreign Application Priority Data

Apr. 18, 1989 [GB] United Kingdom ............... 8908720

[51] Int. Cl.$^5$ .................................. A22B 3/00
[52] U.S. Cl. ............................ 452/198; 452/57; 73/81
[58] Field of Search ............... 452/52, 57, 177, 198; 73/78, 81

[56] References Cited

U.S. PATENT DOCUMENTS

| | | | |
|---|---|---|---|
| 3,593,572 | 7/1971 | Hansen | 73/81 |
| 3,732,727 | 5/1973 | Hinnergardt et al. | 73/81 |
| 3,736,622 | 6/1973 | Wali | 452/177 |
| 3,872,716 | 3/1975 | Hansen | 73/81 |
| 3,956,924 | 5/1976 | Hansen et al. | 73/81 |
| 4,150,374 | 4/1979 | Brook | 452/177 |

OTHER PUBLICATIONS

Soviet Inventions Illustrated Week D 36, 14 Oct. 1981, Derwent Publications, Ltd., London, GB, No. 65562 D/36, D12 S03 & SU-A-745808 (Pacific Ocean Fish) 15 Dec. 1980, (15-12-1980).

Primary Examiner—Willis Little
Attorney, Agent, or Firm—Cushman, Darby & Cushman

[57] ABSTRACT

The degree of rigor in a bird or animal carcass is measured. The carcass is carried on a carrier which runs along a rail and over a slight step or drop, which subjects the carcass to a mechanical shock. A sensor monitors the variation with time of the force exerted by the carcass on the support means which arrests its fall. Circuitry analyzes the response to determine the degree of rigor. The carcass is then subjected to appropriate treatment, e.g., by its further processing being delayed to allow rigor to develop further. This can be done by providing a switch in the rail to route the carcass along a short path or a long path. The particular feature of the response which is monitored by the circuitry may, for example, be the time of fall, the amplitude of oscillation after the carcass has been arrested by the support means, the frequency of that oscillation, the rate at which that oscillation is damped, or some combination of those features.

17 Claims, 2 Drawing Sheets

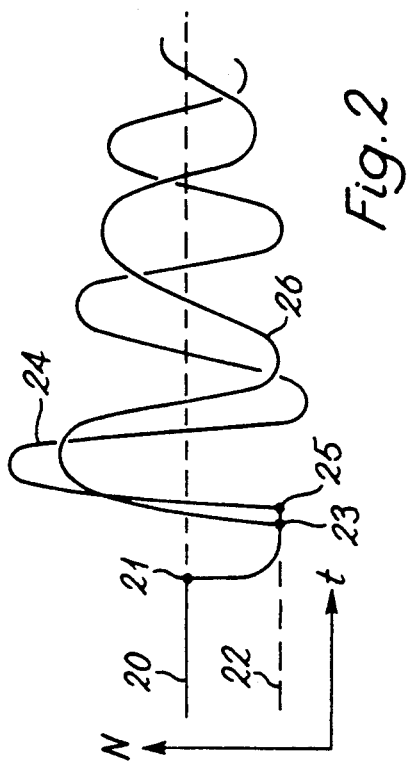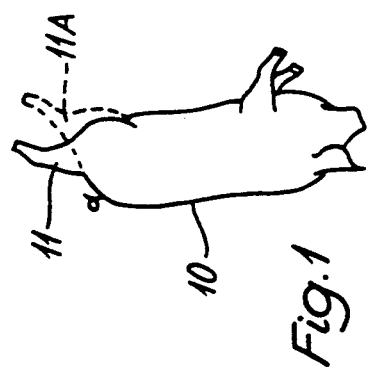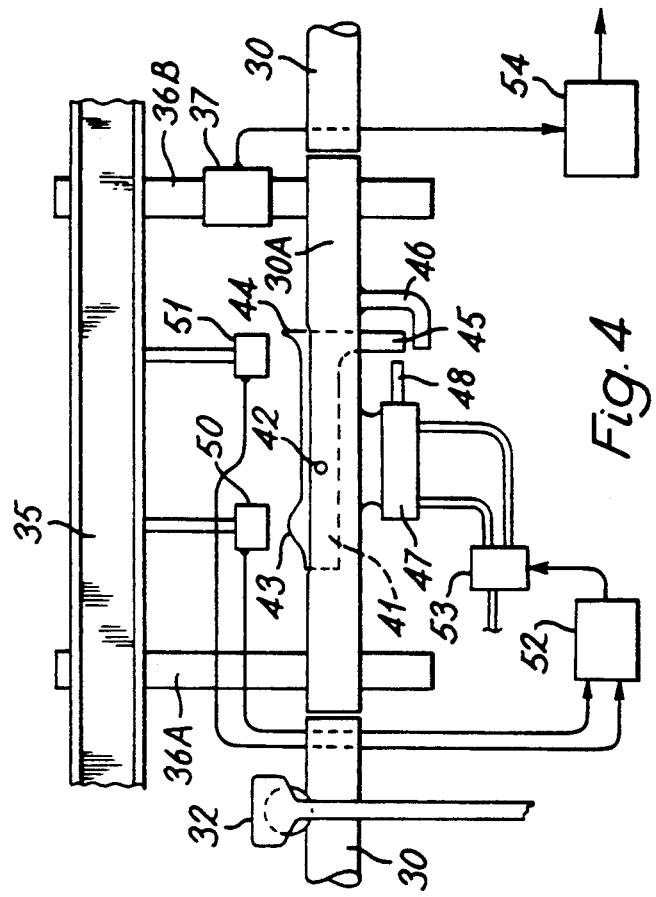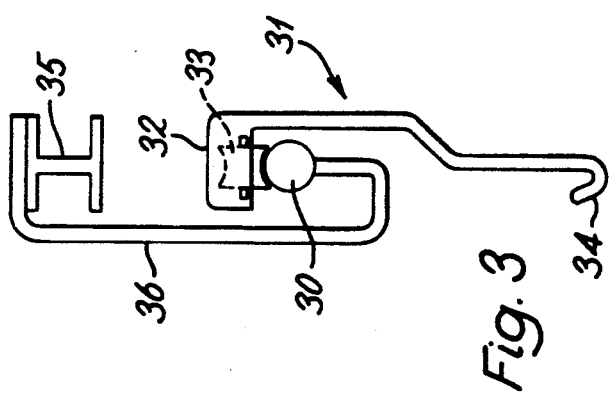

MONITORING MEAT QUALITY

The present invention relates to the monitoring of the quality of meat, and more specifically of animal and bird carcasses during processing shortly after slaughter.

In the process of the slaughter and preparation of poultry, each chicken carcass undergoes an appreciable amount of processing. The bird is first stunned, then killed, and the carcass then undergoes a bleeding period. It is then scalded and passed from the scalding process to a plucking device. From there, it is passed on to further processing, such as chilling, removal of head and feet, removal of giblets, etc. Such processing takes a time of the order of 10 minutes.

There is a considerable variation between carcasses in the changes which occur in them after death. In particular, there is a large variation in the time which a carcass takes to go into rigor. This variability is dependent upon a large number of factors. The genetic make-up of the chicken obviously affects it, but the age of the bird and the manner in which it has been raised also have a considerable effect, and the experience of the bird—the stresses it has undergone—in the period immediately before it is killed also have a major effect. The processing which the carcass undergoes (the method of stunning, the scalding and chilling temperatures, the storage times and temperatures) is also important.

This variation in the time taken by the carcasses to go into rigor has a major effect on the quality of the meat. Carcasses which go into rigor relatively slowly become toughened by cold shortening following cooling (in air or in spin chillers). Conversely, carcasses which go into rigor rapidly become toughened by hot (or rigor) shortening occurring before cooling.

Cold shortening can be alleviated by slow cooling or by electrical stimulation of the carcass soon after stunning. Hot shortening can be alleviated by advancing the time of cooling. However, these measures can only be employed satisfactorily if a suitable technique for measuring rigor is available. In the absence of such a technique, a compromise processing procedure has to be employed, the timing of which is matched to average or typical carcasses. As a result, the quality of carcasses which go into rigor either faster or more slowly than the average carcass will be poorer.

Similar problems arise in the process of the slaughter and preparation of pigs. The stresses which pigs suffer prior to slaughter are highly variable, involving such matters as how gently they are treated, the time taken to transport them to the slaughterhouse, the temperature at which they are kept, and their degree of contact with pigs from other herds during and after transport. A particular problem which occurs with pig carcasses is that of drip; a carcass which goes into rigor rapidly suffers excessive drip, and hence weight loss.

There is therefore a need for a cheap and rapid technique of measuring the development of rigor in animal and bird carcasses. Such a technique would be of substantial utility in the processing of chicken and pig carcasses, but could also find application in the processing of other carcasses, e.g. ducks, turkeys, and cattle.

A considerable number of techniques of measuring rigor have been proposed.

One technique involves excising a muscle and measuring its extensibility; this technique is clearly suitable only for laboratory purposes. Rigor a balloon is measured by inserting into a suitable muscle of the carcass, its resistance to inflation is dependent on the degree of rigor of the muscle. The resilience of the carcass can be measured by placing a spring-loaded penetrometer on a suitable location on the carcass. These procedures however obviously require skilled operators and are hence costly and timeconsuming. With some carcasses, e.g. pigs, the configuration of the carcass (in particular the angle of the front legs) changes with the onset of rigor. Measurement of resilience in these carcasses is difficult, however. With some carcasses, the degree to which the configuration changes if the carcass is rehung (from the hips instead of from the hind legs) also depends on the degree of rigor, but this involves major manipulation of the carcasses, rendering the measurement of the change difficult. Not surprisingly, this technique is not applicable to poultry.

Certain indirect methods of measuring rigor are also known. The onset of rigor is dependent upon the temperature of the animal immediately before it is killed, but the correlation is imperfect, the measurement of the temperature is difficult, and the technique is not applicable to poultry. It is known that the pH of a muscle is related to the development of rigor, and this can be measured by the insertion of a pH sensor into the carcass. The dielectric properties of the muscle also change with the onset of rigor, and can be monitored similarly. The estimation of rigor by the measurement of pH is performed routinely as a laboratory procedure. However, these methods are also unsatisfactory for commercial application, since they involve operator intervention and require the insertion of relatively delicate electrodes into the carcasses.

The primary object of the present invention is therefore to provide a cheap and rapid technique of measuring the development of rigor in animal and bird carcasses.

According to one aspect, the present invention provides a method of measuring the degree of rigor in a carcass, characterized by subjecting the carcass to a mechanical shock and measuring the response of the carcass.

The shock preferably comprises allowing the carcass to fall through a short distance, and the response is preferably measured by monitoring the variation with time of the force exerted by the carcass on the support means which arrest its fall. The particular feature of the response which is monitored may for example be the time of fall, the amplitude of oscillation after the carcass has been arrested by the support means, the frequency of that oscillation, the rate at which that oscillation is damped, or some combination of those features. The function by which the degree of rigor is determined may include the mass of the carcass.

The invention also provides a method of preparing a carcass in which its degree of rigor is so measured and its subsequent treatment is dependent upon its degree of rigor. The degree of rigor may for example adjust the delay in processing, or electrical stimulation of the carcass.

According to another aspect, the invention provides apparatus for determining the condition of a carcass, characterized by a carrier on which the carcass is carried, a rail along which the carrier is moved, means for providing a step in the rail over which the carrier is dropped, and means for measuring the force exerted by the carrier on the rail following the drop.

The step may be formed by two fixed portions of rail at different heights, or by a tiltable element in the rail which is held against rotation under the weight of the carriage as the carriage passes along the rail from one end, and is then released as the carrier nears the other end to allow the carriage to drop. The tiltable element may be controlled by a pneumatic actuator which is in turn controlled by sensors which sense the passage of the carrier past the one end and nearing the other end of the rail.

The apparatus preferably includes computing means for analyzing the measured force on the rail, to determine the time of fall, the amplitude of oscillation after the carcass has been arrested by the support means, the frequency of that oscillation, the rate at which that oscillation is damped, or some combination of those features. The computing means may adjust the criteria used to estimate the degree of rigor according to the weight of the carcass. The computing means may be special-purpose processing circuitry a suitably programmed general-purpose computer, or a combination of both.

The invention also provides apparatus for processing a carcass, comprising apparatus as described for determining the degree of rigor of the carcass, and means for controlling the subsequent processing of the carcass in dependence on its degree of rigor. The subsequent processing may involve controllably delaying the passage of the carcass to subsequent processing, or controllably applying electrical stimulation to the carcass.

An apparatus for determining the condition of a carcass and embodying the invention will be now be described. by way of example, with reference to the drawings. in which:

FIG. 1 shows diagrammatically a suspended pig carcass;

FIG. 2 is two graphs of the response of a carcass to a mechanical shock;

FIG. 3 is an end sectional view of slaughterhouse transport apparatus;

FIG. 4 is a side view of a section of the apparatus of FIG. 3;

FIG. 1 shows a pig carcass in its normal suspended position after slaughter. The carcass is hung by the Achilles tendons, and the hind legs 11 are therefore pulled from their natural position of approximate right angles to the body 10 into the position shown, roughly in line with the body.

Figure 5:
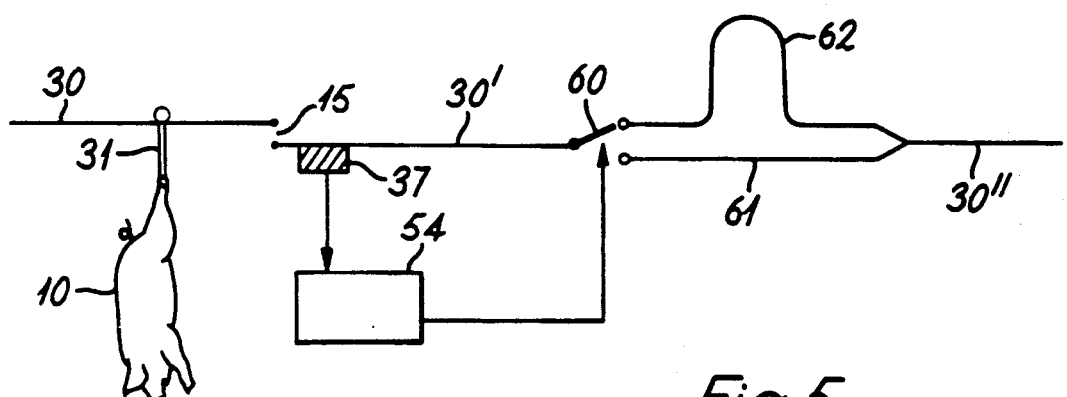
FIG. 5 is a general diagrammatic view of the apparatus.

If the carcass is allowed to drop by a short distance and then arrested, its behavior will depend on the degree to which rigor has developed.

If there is little or no rigor, then when the carcass is released, the tension in the muscles of the hind legs 11 will cause them to return somewhat towards their natural position, as indicated at 11a, during the short period of free fall. The feet will therefore move downwards slightly faster than natural free fall, and will reach the end of the fall distance slightly faster than under natural free fall. When the feet reach the end of the fall distance, the body 10 of the carcass will continue to fall, so stretching the hind legs back to and beyond the position 11. The carcass will then oscillate up and down. The primary frequency of the oscillation will be due mainly to the weight of the bulk of the body and the spring effect of the muscles in the hind legs and, to a lesser extent, the hind quarters of the body; and the decay of the oscillation will be due primarily to the damping effect of the stretching and return of the muscles in the hind legs and hind quarters.

If rigor is well developed, then the carcass will behave more as a single rigid body. When it is released, its rigor (and in particular the rigor of the muscles of the hind legs) will hold the hind legs substantially in the position 11 even though the tension on them is released. When the support carrying the carcass reaches the end of the fall distance, the body 10 will immediately be decelerated. The carcass will then oscillate up and down. The primary frequency of the oscillation will be higher for a carcass with rigor, than for one without because the muscles will have a higher resistance to stretching; and the decay of the oscillation will be slower, because the muscles respond more elastically.

FIG. 2 shows two idealized graphs of the response, with the force N on the support plotted against time t. The initial part 20 of the graphs shows the situation before release of the carcass; this represents the weight of the carcasses. At point 21, the carcasses are released and allowed to fall freely through a fixed distance (a suitable distance is of the order of 50 mm). The graphs therefore drop sharply to the level 22, which represents zero force (i.e. free fall). For the carcass which has developed rigor, the free fall ends sharply at point 25, and an oscillation 26 then follows. For the carcass which has not developed rigor, the free fall ends at an earlier point 23, which is followed by an oscillation 24. Oscillations have been recorded for up to 5 s but typically last for less than 1 s.

It will be seen that the oscillation 24 for the carcass without rigor is of a lower frequency (typically around 7 Hz for a pig carcass) than that (typically around 15 Hz) for oscillation 26 for the carcass with rigor. Also, the damping of the oscillation 26 is higher than for the oscillation 24. (The damping is normally measured per cycle; the higher frequency of the oscillation 26, with lower damping, means that the envelopes of the two oscillations 24 and 26 are not markedly different.)

It will be realized that the amplitudes of the graphs will increase if the weight of the carcass is increased, while the frequencies will correspondingly decrease.

FIG. 5 is a general view of typical slaughterhouse transport apparatus. Carcasses 10 are carried on carriers 31 which run along a rail 30 to carry them through various stages of processing. A step or drop 15 is provided in the rail, and a sensor 37 senses the force on the rail which is transmitted thereto via the carrier 31 from the carcass 10 as it goes over the drop 15. The sensor feeds signal processing circuitry 54 which determines the degree of rigor in the carcass by monitoring the variation with time of the force exerted by the carcass on the rail 30 as it drops down the step or drop 15.

The processing of the carcass is controlled in dependence on its rigor. Thus a diverting section may be provided in the rail 30 between the sections 30' and 30", comprising a switch 60 and two parallel sections 61 and 62 of different lengths. The time of travel of the carcass 10 along the track depends on the setting of the switch 60, which is controlled by the circuitry 54.

FIG. 3 is an endwise sectional view of typical slaughterhouse transport apparatus. The rail 30 is a tubular rail which supports a series of carcass carriers 31 which can be moved along it. (The carriers are usually moved along the rail by means of a continuously driven chain arrangement (not shown) above the rail. with which the carriers engage.) Each carrier has a housing 32 containing a wheel 33 at its upper end, and a hook 34 at its lower end from which the carcass is hung. The rail 30 is supported from a beam 35 by means of C-shaped brackets 36 located at suitable intervals along the rail; the brackets may be welded to the rail 30 and bolted to the beam 35.

FIG. 4 is a simplified and diagrammatic side view of a section of the rail 30 incorporating means for subjecting a carcass on a carrier 31 to a mechanical shock and measuring the response.

The rail 30 includes a separate section 30A which is isolated from the rest of the rail, and is supported by two brackets 36A and 36B; the right-hand bracket 36B incorporates a strain gauge 37 which senses the weight supported by that bracket. The rail section 30A has a longitudinal slot cut along its top, and a tiltable plate 41 is pivoted at 42 inside the slot as shown. The plate 41 has a hump 43 on its top surface to the left of the pivot 42 and a cusp 44 at its right-hand end, and a toe 45 projecting downwards through a hole in the bottom of the rail 30A as shown. A stop 46 is attached underneath the rail 30A adjacent to the hole through which the toe 45 projects, and a pneumatic actuator 47 is attached underneath the rail 30A so that its armature 48 will be interposed between the toe 45 and the stop 46 in the extended position.

Two sensors 50 and 51, connected to a control unit 52, are mounted below the beam 35 at positions where they sense the passage of a carrier 31 on the hump 43 and at the cusp 44 respectively of the plate 41.

The operation is as follows.

As a carrier 31 is moved along the rail 30, from left to right, it passes onto the rail section 30A, and then runs onto the left-hand end of the plate 41. It then runs onto the hump 43, so pressing the left-hand end of the plate 41 downwards and raising its right-hand end. The carrier is sensed by sensor 50 at this point, and control unit 52 causes a pneumatic control unit 53 to operate the actuator 47 to extend its armature 48 to lie between the toe 45 and the bracket 46, so locking the plate 41 in the raised position.

As the carrier 31 is moved onwards, it runs up the plate 41 to reach the cusp 44, which briefly halts its progression. The carrier is sensed by sensor 51 at this point, and control unit 52 causes a pneumatic control unit 53 to operate the actuator 47 to withdraw its armature 48 from between the toe 45 and the bracket 46. The plate 41 is thereby released, and drops back to its original position, the carrier 31 dropping with it. A carcass hung from the carrier 31 will thereby drop and exert a varying force on the rail 30A, as discussed above, when its drop from the raised end of plate 41 ends as the carrier reaches the main body of the rail 30A. This force is sensed by the strain gauge 37.

The strain gauge 37 feeds the signal analyzer unit 54, which analyzes the resulting oscillation to determine the time of fall, the amplitude of the ensuing oscillation, the frequency of oscillation, the rate at which the oscillation is damped, or some combination of those features. From these factors, a measure of the extent to which rigor has developed in the carcass is calculated. The weight of the carcass can also be determined, and used to adjust the calculation.

The signal from the strain gauge 37 is likely to contain noise from various sources, such as high frequencies from higher mode oscillations of the carcass and low frequencies from pendulum oscillations of the carcass. The analyzer unit therefore preferably includes means for frequency filtering. e.g. by taking Fourier transforms. The analyzer unit 54 may be special-purpose processing circuitry a suitably programmed general-purpose computer, or a combination of both.

Figure 6:
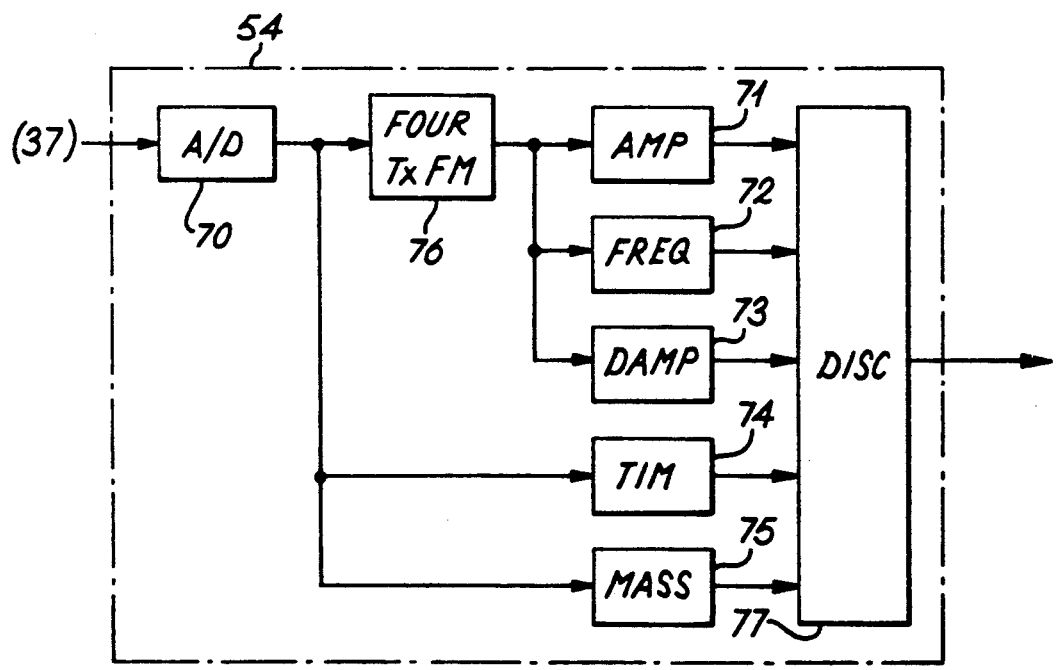
FIG. 6 is a block diagram of the signal processing circuitry of the apparatus.

FIG. 6 is a block diagram of the main functional components of a generalized form of the circuit 54. The signal from the sensor 37 is converted to digital form by an analog-to-digital converter 70, and fed to five discriminator units 71 to 75—an amplitude discriminator 71, a frequency discriminator 72, a damping discriminator 73, a timing discriminator 74, and a mass discriminator 75. These five units feed a combining circuit 77 which determines the rigor of the carcass in dependence on the amplitude, frequency, damping, and timing of the signal from the sensor 37 and the mass of the carcass (the mass being determined by the DC level of the signal after the drop). The units 71 to 73 are preferably fed from the converter 70 via a Fourier transform circuit 76.

It will be understood that the rigor may be determined as either a set of discrete values (of only 2 possible values in the extreme) or a continuously variable value.

A time delay could be used instead of the sensor 51 to determine the moment of release and drop of the plate 41 after the carrier 31 has passed the sensor 50.

The sensors 50 and 51, the actuator 47, and any ancillary components must be chosen to withstand the conditions encountered in abattoirs, in particular the use of steam cleaning, and to comply with the usual hygiene requirements.

It is possible to use a simple fixed step in the rail 30 instead of the arrangement described. However, the start of the drop of a carrier from a fixed step is less definite, and not easily timed. Thus with a fixed step, the time of fall could not easily be measured, and there might also be some degradation of the quality of the resulting oscillations.

The actuator 47 is preferably a double-acting one, in which the extension and retraction of the armature 48 are both positively driven. However, a spring-operated extension could be used, since there is no substantial load on the actuator when the toe 45 of the plate 41 is raised.

The mechanical layout of the components can obviously be varied without affecting the principles of operation.

With poultry, the usual sequence of processing stages consists of stunning, killing, bleeding, scalding, plucking, followed by various stages of butchering, chilling, and packing. The present apparatus can be located at a variety of points in this processing, e.g. during bleeding, between bleeding and scalding, between scalding and plucking (a position which we believe to be particularly suitable), or after plucking. It will be noted that the development of rigor can be determined before plucking.

The present apparatus provides an indication of the degree of development of rigor of each carcass, and this indication can usefully be used to control the subsequent processing of the carcass. For example, carcasses in which rigor is developing relatively slowly can be shunted onto longer tracks so that all carcasses have reached substantially the same degree of rigor by the time they reach the chilling stage, or electrical stimulation can be applied to the carcasses with the degree of stimulation being inversely proportional to the rate of development of rigor.

The same principle of feed-forward control, varying the precise details of the processing of carcasses in dependence on the degree of rigor development in them, can obviously be applied to other species, such as pigs.

I claim:

1. A method of measuring the degree of rigor in a carcass, characterized by subjecting the carcass to a mechanical shock and measuring the response of the carcass.

2. A method according to claim 1, characterized in that the shock consists of allowing the carcass to fall through a short distance.

3. A method according to either previous claim, characterized in that the response is measured by monitoring the variation with time of the force exerted by the carcass on the support means which arrest its fall.

4. A method according to claim 3, characterized in that the degree of rigor is determined as a function of the time of fall, the amplitude of oscillation after the fall of the carcass has been arrested, the frequency of that oscillation, and/or the rate at which that oscillation is damped.

5. A method according to claim 4, characterized in that the function by which the degree of rigor is determined includes the mass of the carcass.

6. A method of preparing a carcass characterized in that its degree of rigor is measured as described in any either of claims 1 or 2 and its subsequent treatment is dependent on its degree of rigor.

7. A method according to claim 6 characterized in that the passage of the carcass to subsequent processing is delayed in dependence on its rigor.

8. A method according to claim 6, characterized in that the carcass is electrically stimulated in dependence on its rigor.

9. Apparatus for determining the condition of a carcass, characterized in that it comprises a carrier on which the carcass is carried, a rail along which the carrier is moved, means for providing a step in the rail over which the carrier is dropped, and means for measuring the force exerted by the carrier on the rail following the drop.

10. Apparatus according to claim 9, characterized in that the step is formed by two fixed portions of rail at different heights.

11. Apparatus according to claim 9, characterized in that the step is formed by a tiltable element in the rail which is held against rotation under the weight of the carriage as the carriage passes along it from one end, and is then released as the carrier nears the other end to allow the carriage to drop.

12. Apparatus according to claim 11, characterized in that the tiltable element is controlled by a pneumatic actuator which is in turn controlled by sensors which sense the passage of the carrier past the one end and nearing the other end.

13. Apparatus according to any of claims 9 to 12, characterized in that it includes means for determining the degree of rigor from the measured force on the rail as a function of the time of fall, the amplitude of oscillation after the carcass has been arrested by the support means, the frequency of that oscillation, and/or the rate at which that oscillation is damped.

14. Apparatus according to claim 13, characterized in that the degree of rigor is determined by said means as a function also of the mass of the carcass.

15. Apparatus for processing a carcass, characterized by apparatus according to any one of claims 9-12 for determining the degree of rigor of the carcass, and means for controlling the subsequent processing of the carcass in dependence on its degree of rigor.

16. Apparatus according to claim 15, characterized by means for controllably delaying the passage of the carcass to subsequent processing.

17. Apparatus according to claim 15, characterized by means for controllably applying electrical stimulation to the carcass.

* * * * *